United States Patent [19]

Immler et al.

[11] 4,187,305
[45] Feb. 5, 1980

[54] PROCEDURE FOR TREATING MAMMALS TO CONTROL PARASITIC DIPTERA LARVAE

[75] Inventors: Rolf Immler, Arisdorf; Hans Bouvard, Ollon, both of Switzerland

[73] Assignee: Ciba-Geigy Corporation, Ardsley, N.Y.

[21] Appl. No.: 10,279

[22] Filed: Feb. 7, 1979

[30] Foreign Application Priority Data

Feb. 17, 1978 [CH] Switzerland ............... 1762/78

[51] Int. Cl.² .................................... A61K 31/53
[52] U.S. Cl. ............................................ 424/249
[58] Field of Search .................................. 424/249

[56] References Cited

PUBLICATIONS

Brechbuhler et al., Chem. Abst., vol. 88 (1978) p. 152,673b.

*Primary Examiner*—Sam Rosen
*Attorney, Agent, or Firm*—Frederick H. Rabin

[57] ABSTRACT

The present invention relates to a procedure for treating domestic animals and productive livestock belonging to the class of Mammalia (mammals) for systemic control of tissue-parasitic insect larvae of the order of Diptera, which comprises peroral administration, to the animals to be treated, of an effective dose of an active substance of the general formula I

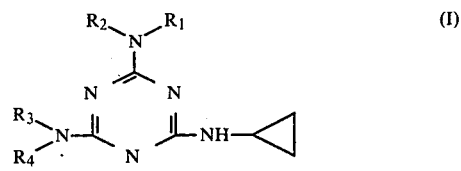

in which $R_1$ is hydrogen, methyl, ethyl or cyclopropyl, $R_2$ is hydrogen or methyl, $R_3$ is hydrogen, methyl or cyclopropyl and $R_4$ is hydrogen or methyl, or of an acid addition salt thereof which is non-toxic to mammals or of a composition which contains the active substance or an acid addition salt thereof which is non-toxic to mammals.

5 Claims, No Drawings

PROCEDURE FOR TREATING MAMMALS TO CONTROL PARASITIC DIPTERA LARVAE

The present invention relates to a procedure for treating domestic animals and productive livestock belonging to the class of Mammalia (mammals) for systemic control of tissue-parasitic insect larvae of the order of Diptera, which comprises peroral administration, to the animals to be treated, of an effective dose of an active substance of the general formula I

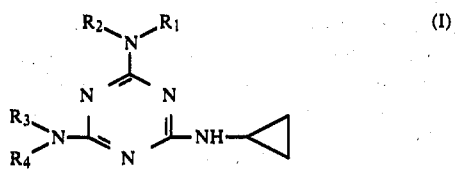

in which $R_1$ is hydrogen, methyl, ethyl or cyclopropyl, $R_2$ is hydrogen or methyl, $R_3$ is hydrogen, methyl or cyclopropyl and $R_4$ is hydrogen or methyl, or of an acid addition salt thereof which is non-toxic to mammals or of a composition which contains the active substance or an acid addition salt thereof which is non-toxic to mammals.

The term acid addition salts of compounds of the formula I is to be understood as meaning salts with pharmaceutically acceptable acids, for example with strong mineral acids, such as hydrochloric acid or sulfuric acid, or with organic acids, such as acetic acid, tartaric acid or citric acid.

Amongst the compounds of the formula I, 2,4-diamino-6-cyclopropylamino-s-triazine is very particularly suitable for control of tissue-parasitic insect larvae of the order of Diptera, because of its outstanding action.

The control of Diptera larvae, which live as parasites in the tissues of their host animals, is of extremely great importance, especially in view of the considerable damage which can be caused by the parasites in productive livestock husbandry and very particularly in the husbandry of grazing animals.

The Diptera larvae can find their way into the tissues of their host animals in very diverse ways. Thus, after oviposition by the Diptera females, which can take place at various parts of the body of the host animals, the larvae hatched from the eggs can be taken in by the host animals by licking and bore into the pharynx, or the larvae can bore into the skin of the host animals from the outside. However, the eggs can also first be deposited on mosquitoes or flies. The larvae develop in the eggs and hatch as soon as the carrier insect seeks out a suitable host animal. In the case of the viviparous Diptera species the larvae can be introduced direct by the Diptera females into the nose or the eyes of the host animals.

After the larvae have passed into the host animals, they can, by migration, seek out those parts of the body which they prefer. The larvae can be present, for example, in or under the skin, in the gastro-intestinal tract or in the nasal cavities, the cavity of the pharynx or the frontal sinus of their hosts.

The various types of parasitism by Diptera larvae in animals are termed myiases.

Myiases can occur in numerous species of animals, for example in cattle, horses, donkeys, mules, reindeer, sheep, pigs, dogs and cats.

In the host animals, the infestation by parasitic Diptera larvae can lead, in addition to other adverse effects, to a reduction in the milk yield, to loss of wool, loss of weight or even to death. If the host animals are infested by skin parasites which cause swellings to form in the skin, this can also result in depreciation in the value of the skins due to perforation, since the swellings have a small orifice which is enlarged by the larvae before they leave the host for pupation.

Since the larvae can infest very diverse parts of the body of the host animals, some of which parts are not readily accessible, their control is highly problematical.

It has now been found that, surprisingly, compounds of the formula I and compositions which contain these compounds as active ingredients, are outstandingly suitable for the control of parasitic Diptera larvae. The substances develop a systemic action which means that on peroral application to the host animal an action against the parasitic Diptera larvae takes place even in parts of the body which have not been treated. The procedure according to the invention thus enables parasitic Diptera larvae to be effectively controlled even in those parts of the body in which direct application is extremely difficult or virtually impossible.

The compounds of the formula I and their acid addition salts which are non-toxic to mammals are advantageously used in a concentration in the range of 1 to 20 mg/kg of body weight.

A particularly advantageous method for control of the parasites comprises providing the animals to be treated with the active substance as a constituent of licks or administering to them a formulation which effects release of the active substance in the rumen.

The use of licks which contain the active substance proves particularly advantageous in the treatment of large herds living outdoors, in which case individual treatment of the animals is laborious and time-consuming.

The advantage of a formulation which effects release of the active substance in the rumen is that the active substance is released slowly and thus develops its action over a prolonged period of time.

Furthermore, the application of the active substance by spraying a liquid formulation into the oesophagus of the animals to be treated, using a suitable applicator (drench gun), also proves very advantageous.

The compounds of the formula I have, in particular, a good action against myiasis-producing larvae of insects of the order Diptera, which belong to the families Calliphoridae, Oestridae, Cuterebridae, Gasterophilidae, Sarcophagidae and Hypodermatididae, for example against larvae of Lucilia spec., *Cochlyomyia hominivorax, Chrysomyia bezziana, Hypoderma lineata, Hypoderma bovis, Dermatobia hominis, Oedemagena tarandi*, Gasterophilus spec., *Oestrus ovis, Rhinoestrus purpureus, Wohlfahrtia vigil* and Cuterebra spec.

The compounds of the formula I can be prepared according to processes known per se, by, for example, (a) reacting a 2-cyclopropylamino-4-amino-6-halogeno-s-triazine of the formula II, in which $R_1$ and $R_2$ are as defined for formula I and X is halogen, preferably chlorine, with ammonia or a primary and/or secondary amine of the formula V, in which $R_3$ and $R_4$ are as defined for formula I:

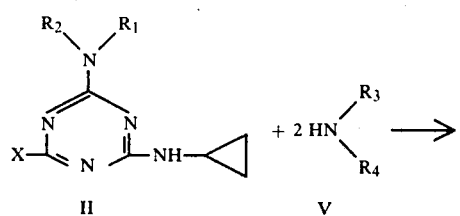

II    V

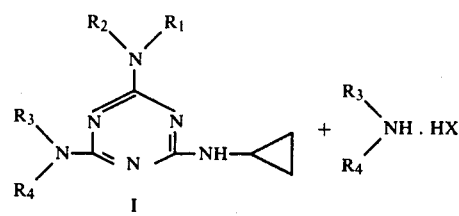

I or (b) reacting a 2,4-diamino-6-halogeno-s-triazine of the formula III, in which $R_1$, $R_2$, $R_3$ and $R_4$ are as defined for formula I and X is halogen, preferably chlorine, with cyclopropylamine (formula VI):

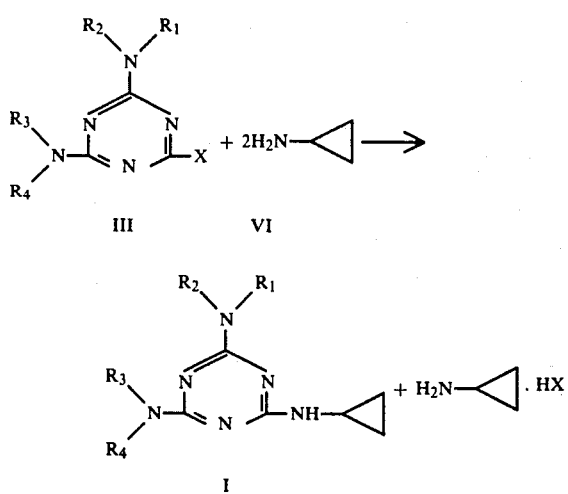

III    VI

I or (c) if, in the compounds of the formula I, $R_1$ has the same meaning as $R_3$ and $R_2$ has the same meaning as $R_4$, reacting a 2-cyclopropylamino-4,6-dihalogeno-s-triazine of the formula IV, in which X is halogen, preferably chlorine, with ammonia or a primary and/or secondary amine of the formula VII, in which $R'_1$ has the meaning defined for $R_1=R_3$, as indicated for formula I, and $R'_2$ has the meaning defined for $R_2=R_4$, as indicated for formula I:

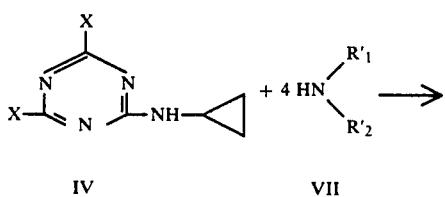

IV    VII

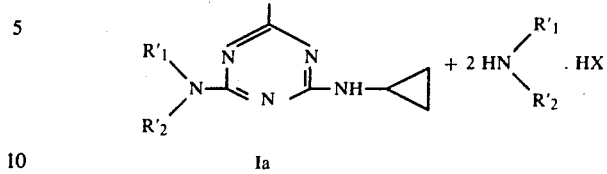

Ia

The replacement of the halogen atoms by ammonia or primary and/or secondary amines of the formulae V, VI and VII takes place by dissolving the starting materials of the formulae II, III and IV in inert solvents, for example acetone, acetone/water mixtures, methyl ethyl ketone, dioxan or dioxan/water mixtures, and reacting these mixtures under normal or, if desired, elevated pressure and at temperatures of 20°–150° C. and preferably 50°–140° C. with ammonia or primary and/or secondary amines.

The starting materials of the formulae II, III and IV are known in most cases or can be prepared analogously to known processes.

EXAMPLE 1

(a) 2-Cyclopropylamino-4,6-diamino-s-triazine

A mixture of 100 g of 2-cyclopropylamino-4-amino-6-chloro-s-triazine, 51 g of ammonia and 500 ml of dioxan is heated at 140° C. in an autoclave for 24 hours. After cooling, the dioxan is removed by filtering with suction in vacuo and the crystalline residue is washed with water and dried. The crude product is recrystallised from methanol; melting point 219°–222° C.

(b) 2-Cyclopropylamino-4,6-diamino-s-triazine, salt with 2 mols of hydrochloric acid 25 g of 2-cyclopropylamino-4,6-diamino-s-triazine are dissolved in 2,000 ml of hot absolute ethanol. This solution is cooled to 15° C. and cooled further with ice and hydrogen chloride gas is then passed in until the solution is saturated. White crystals precipitate out. These are filtered off and the crude salt thus obtained is washed with a large amount of ether; melting point 195° C. (decomposition).

EXAMPLE 2

(a) 2-Cyclopropylamino-4-methylamino-6-amino-s-triazine

A mixture of 12.7 g of 2-cyclopropylamino-4-methylamino-6-chloro-s-triazine, 17.4 g of 28% aqueous ammonia solution and 30 ml of dioxan is heated at 140° C. in an autoclave for 4 hours. After cooling, the reaction mixture is poured into 350 ml of a solution, which has been cooled to 0° C., of potassium carbonate in water and extracted with 1:1 benzene/ether. After drying over sodium sulfate, the solvents are removed in vacuo and the residue is recrystallised from isopropanol/hexane; melting point 159°–162° C.

(b) 2-Cyclopropylamino-4-methylamino-6-amino-s-triazine, salt with 2 mols of hydrochloric acid 38 g of 2-cyclopropylamino-4-methylamino-6-amino-s-triazine are dissolved in 280 ml of chloroform. This solution is cooled with ice to 0°–5° C. and hydrogen chloride gas is passed in until the solution is saturated.

White crystals precipitate out. 280 ml of ether are added to bring the precipitation to completion. The crude hydrochloride is filtered off and recrystallised from methanol; melting point 197°–199° C.

EXAMPLE 3

2,4,6-Tris-cyclopropylamino-s-triazine

A mixture of 20 g of 2-chloro-4,6-bis-cyclopropylamino-s-triazine, 10.1 g of cyclopropylamine and 80 ml of dioxan is heated at 140° C. in an autoclave for 22 hours. The reaction mixture is concentrated in vacuo to half its volume and 300 ml of water are added. The mixture is extracted with ethyl acetate, the product phase is dried over sodium sulfate and the solvents are removed in vacuo. The residue is recrystallised from dioxan/petroleum ether; melting point 75°–77° C.

The following compounds of the formula I can, for example, also be prepared in a manner analogous to that in Examples 1 to 3:

| No. | Compound | Melting point in ° C. |
|---|---|---|
| 1 | 2-cyclopropylamino-4-amino-6-dimethyl-amino-s-triazine | 182–184 |
| 2 | 2,4-bis-(cyclopropylamino)-6-amino-s-triazine | 137–140 |
| 3 | 2-cyclopropylamino-4-methylamino-6-dimethylamino-s-triazine dihydrochloride | 164–165 |
| 4 | 2-cyclopropylamino-4,6-bis-(dimethyl-amino)-s-triazine | 140–142 |
| 5 | 2-cyclopropylamino-4-amino-6-ethylamino-s-triazine | 141–145 |
| 6 | 2-cyclopropylamino-4-amino-6-ethylamino-s-triazine dihydrochloride | 199–200 |
| 7 | 2,4-bis-(cyclopropylamino)-6-dimethyl-amino-s-triazine | 136–137 |

The compounds of the formula I or their acid addition salts which are non-toxic to mammals can be used as pure active substance or together with suitable carriers and/or adjuvants. Suitable carriers and adjuvants can be solid or liquid and are the substances conventionally employed in the art of formulation, for example natural or regenerated substances, solvents and/or dispersants.

Depending on the use, the active substances can be administered in the form of solutions, emulsions, wettable powders, suspensions, granules, pellets, bolusses, tablets or capsules. The active substances or compositions containing these can, however, also be added to the feed or drink or can be contained in a premix. The active substances can, for example, be combined with adjuncts such as kaolin, lime, aluminium oxide, ground mussel shells, bolus alba, aerosil, starch or lactose, talc, bentonite, sodium chloride, calcium phosphate, cottonseed meal or liquids which are inert towards the active substances, such as oils and other solvents and diluents harmless to the animals to be treated.

The active substances can also be administered, to the animals to be treated, as a constituent of licks.

The use of a formulation which effects release of the active substance or of a non-toxic acid addition salt thereof in the rumen is particularly suitable for slow release of the active substance.

The active substances of the formula I or their non-toxic acid addition salts can be processed to the following formulations.

Granules:

5 parts of active substance are dissolved in a solvent such as methylene chloride and the solution is mixed with 2 parts of polyethylene glycol ("carbowax"). 91.5 parts of calcium carbonate are impregnated with the mixture and 1.5 parts of precipitated silica are mixed in and the solvent is then evaporated.

Wettable powder:

50 parts of active substance are mixed with 5 parts of a dispersant, for example sodium ligninsulfonate, 5 parts of a wetting agent, for example dibutylnaphthalenesulfonic acid, 10 parts of silica and 30 parts of kaolin and the mixture is finely ground.

Emulsifiable concentrate:

20 parts of active substance are mixed with 20 parts of emulsifier, for example a mixture of alkylaryl polyglycol ether and alkylarylsulfonates, and 60 parts of solvent, until the solution is completely homogeneous. With water, this concentrate gives an emulsion of any desired concentration.

Premix: (Feed additive)

5 parts of active substance and 5 parts of secondary calcium phosphate, or kaolin, aerosil or carbonated lime, are mixed homogeneously with 90 parts of a feed, for example feed concentrate.

Solutions (for dilution with drinking water)

(a) 15% active substance in "Solketal ®" (2,2-dimethyl-4-hydroxymethyl-1,3-dioxolane)

(b) 10% active substance in "Carbitol ®" (diethylene glycol monethyl ether)

10% active substance in polyethylene glycol 300

(d) 5% active substance in glycerol

Soluble powder 25 parts of active substance
1 part of Tensopol SP-USP (sodium lauryl-sulfate USP)
3 parts of colloidal silica K 320
71 parts of urea The constituents are mixed and the mixture is ground finely in a suitable mill.

Other biocidal active substances or agents, which are inert towards the active substances and acceptable to the animals to be treated, or mineral salts or vitamins can be admixed to the compositions described.

TEST

Peroral use in sheep and cattle

An active substance of the formula I is administered perorally in an amount of 5 mg/kg of body weight in a suitable formulation to sheep and cattle, using a "drench gun". The animals treated are artifically infested with larvae of Lucilia sericata. The larvicidal action is assessed after 72 hours.

In this test, compounds of the formula I show a pronounced larvicidal action.

What is claimed is:

1. A procedure for treating domestic animals and productive livestock belonging to the class of Mammalia for systemic control of tissue-parasitic insect larvae of the order of Diptera, which comprises peroral administration, to the aminals to be treated, of an effective dose of an active substance of the general formula I

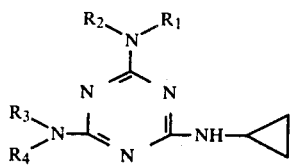

(I)

in which $R_1$ is hydrogen, methyl, ethyl or cyclopropyl, $R_2$ is hydrogen or methyl, $R_3$ is hydrogen, methyl or cyclopropyl and $R_4$ is hydrogen or methyl, or of an acid addition salt thereof which is non-toxic to mammals or of a composition which contains the active substance or an acid addition salt thereof which is non-toxic to mammals.

2. A procedure according to claim 1, wherein the active substance used is 2,4-diamino-6-cyclopropylamino-s-triazine.

3. A procedure according to claim 1, wherein the application is made by administering, to the animals to be treated, a formulation which effects release of the active substance, or of an acid addition salt thereof which is non-toxic to mammals, in the rumen.

4. A procedure according to claim 1, wherein the application is made by using licks which contain the active substance or an acid addition salt thereof which is non-toxic to mammals.

5. A procedure according to claim 1, wherein the application is made by spraying a liquid formulation into the oesophagus of the animals to be treated, using a suitable applicator.

* * * * *